United States Patent
Shiloach et al.

(10) Patent No.: US 8,017,566 B2
(45) Date of Patent: Sep. 13, 2011

(54) LIQUID PERSONAL CLEANSING COMPOSITION

(75) Inventors: Anat Shiloach, Trumbull, CT (US); Suzanne Lynn Gencarelli, Milford, CT (US); Sirisha Muppidi, Trumball, CT (US); Michael A. Rahn, New York, NY (US); Rosa Mercedes Paredes, Shelton, CT (US)

(73) Assignee: Conopco, Inc., Englewood Cliffs, NJ (US)

(*) Notice: Subject to any disclaimer, the term of this patent is extended or adjusted under 35 U.S.C. 154(b) by 0 days.

(21) Appl. No.: 12/618,145

(22) Filed: Nov. 13, 2009

(65) Prior Publication Data

US 2011/0118162 A1    May 19, 2011

(51) Int. Cl.
*C11D 3/37* (2006.01)
*C11D 3/20* (2006.01)
*C11D 1/02* (2006.01)
*C11D 9/26* (2006.01)

(52) U.S. Cl. ........ 510/119; 510/123; 510/127; 510/159; 510/426; 510/434; 510/437; 510/438; 510/476; 510/477; 510/488; 424/487; 424/70.16; 424/70.22

(58) Field of Classification Search .......... 510/119, 510/123, 127, 159, 426, 434, 437, 438, 476, 510/477, 488; 424/487, 70.16, 70.22
See application file for complete search history.

(56) References Cited

U.S. PATENT DOCUMENTS

| | | | |
|---|---|---|---|
| 4,830,774 | A | 5/1989 | LaPetina et al. |
| 5,716,920 | A | 2/1998 | Glenn, Jr. et al. |
| 5,869,070 | A | 2/1999 | Dixon et al. |
| 5,885,948 | A | 3/1999 | Glenn, Jr. et al. |
| 6,191,083 | B1 | 2/2001 | Brooks et al. |
| 6,444,629 | B1 | 9/2002 | Elliott et al. |
| 7,410,649 | B2 | 8/2008 | Yoshimi et al. |
| 2004/0087668 | A1 | 5/2004 | Schmucker-Castner et al. |
| 2007/0161524 | A1 | 7/2007 | Counradi et al. |
| 2009/0075857 | A1* | 3/2009 | Jonke et al. .......... 510/337 |
| 2009/0221463 | A1 | 9/2009 | Kitko et al. |
| 2010/0035783 | A1* | 2/2010 | Restrepo et al. ........ 510/159 |

FOREIGN PATENT DOCUMENTS

| | | |
|---|---|---|
| WO | 95/13355 A1 | 5/1995 |
| WO | 98/04239 | 2/1998 |
| WO | 2005/094781 A1 | 10/2005 |
| WO | WO 2006/102978 * | 10/2006 |

OTHER PUBLICATIONS

International Search Report, PCT/EP2010/068563, mailed Feb. 17, 2011, 3 pp.

* cited by examiner

*Primary Examiner* — Brian P Mruk
(74) *Attorney, Agent, or Firm* — Alan A. Bornstein (57) ABSTRACT

A mild, substantially isotropic skin cleansing solution was found to be able to suspend insoluble components and provide copious amounts of lather. The cleanser is formulated with synthetic anionic surfactants and a specific ratio of carboxylic acid(s) to hydrophobically modified cross-linked acrylate copolymer(s). The carboxylic acid and acrylate polymer combination were found to provide a synergistic effect on zero shear viscosity at 25 C in a specific pH and copolymer/acid concentration ratio range.

9 Claims, 1 Drawing Sheet

LIQUID PERSONAL CLEANSING COMPOSITION

BACKGROUND OF THE INVENTION

1. Field of the Invention

The present invention relates to liquid cleansing compositions suitable for topical application for cleansing the human body, such as the skin and hair. In particular, it relates to a stable, substantially isotropic and finely dispersed oil free personal cleansing composition that is able to suspend appreciable levels of insoluble ingredients and produce copious lather.

2. Background of the Art

Commercially available liquid personal cleansing compositions such as shower gels, facial and hand cleansers are generally applied to cleanse the skin. The lather such products produce is an important sign to the user that the product is working while providing pleasant sensory effects. Another important attribute of the product to the user is the visual appearance which can help communicate various benefits through the addition of particles such as opacifiers, mica, beads, oils etc. that are visible to the user.

Isotropic liquid cleansers are known that have hydrophobic emollient oils. U.S. Pat. No. 6,001,344 issued on Dec. 14, 1999 to Villa et al. discloses an isotropic cleansing composition having large oil droplets in the 1 to 500 micron range average diameter.

U.S. Pat. Nos. 5,854,293 and 6,066,608 issued on Dec. 29, 1998 and on May 23, 2000 to Glenn Jr. respectively disclose a moisturizing liquid personal cleansing emulsion with at least 10% of its lipophilic skin moisturizing agent droplets having a diameter of greater than 200 microns with an analytical range of detection of up to 1000 microns.

U.S. Pat. No. 5,965,500 issued on Oct. 12, 1999 to Puvvada discloses a stable, isotropic liquid cleansing composition containing high levels of emollients equal to or in excess of the surfactant level. The composition further contains C2-C24 carboxylic acids and/or cationic polymers in a preferred embodiment.

U.S. Pat. No. 5,661,189 issued on Aug. 26, 1997 to Grieveson et al. discloses an isotropic, aqueous liquid cleansing and moisturizing composition with a thickened benefit agent having a weight average particle size in the range of 50 to 500 microns and an optional structuring agent selected from clays, carboxylic acids and derivatives thereof, cross-linked polyacrylates, polyvinylpyrrolidone, natural gums, polysaccharide derivatives, polyols, polyol esters and inorganic salts.

U.S. Pat. No. 7,098,180 issued on Aug. 29, 2006 to Ganopolsky et al. discloses an isotropic cleansing composition containing anionic and amphoteric surfactants, and a hydrophobically modified crosslinked, anionic acrylic copolymer.

U.S. Patent Publication No. 2004/0121925 published on Jun. 24, 2004 to Harmalker discloses a stable isotropic cleansing composition containing anionic and amphoteric surfactants, xanthan and guar gum thickeners, and dispersed phase suspended particles of conditioning agents in the 200-2500 micron diameter range and with a clarity of less than or equal to 20 NTU of the continuous phase absent the particles. The particles consist of gums, gelatins or the like and may contain oil(s) within the particles.

U.S. Pat. No. 7,084,104 issued on Aug. 1, 2006 to Martin et al. discloses an isotropic cleansing composition containing anionic and amphoteric surfactants, a hydrophobically modified crosslinked, anionic acrylic copolymer thickener, volatile silicone conditioners and humectants.

U.S. Pat. No. 6,191,083 issued on Feb. 20, 2001 to Brooks, et al. discloses cleansing compositions with thickening systems that comprise an associative polymer and a polar oil.

U.S. Pat. No. 5,869,070 issued on Feb. 9, 1999 to Dixon et al. discloses cleansing compositions stabilized by specific gel-forming polymers containing a lipid moisturizing agent.

U.S. Patent Publication No. 2007161524 published on Jul. 12, 2007 to Counradi, Katrin; et al. discloses foaming cleansing solutions comprising anionic surfactants, gel-forming acrylate thickeners and a mixture of ethoxylated mono, di, and triglycerides of C8-C22 carboxylic acids.

As discussed in these and other prior art references, it is known to use carboxylic acids and acrylate copolymers either separately or together to structure anionic surfactant cleansing compositions. However it was surprisingly discovered that specific carboxylic acids and specific crosslinked acrylates form a synergistic combination to affect zero shear viscosity at 25 C substantially beyond what would be expected from the simple combination of the two. Moreover, unexpected copious and creamy lather creation of the inventive compositions was seen to be a side benefit. In addition, the enhanced suspending ability at increased zero shear viscosity levels for insoluble components such as beads, particles and large oil droplets above 500 or 1000 microns average diameter was another synergistic benefit.

BRIEF DESCRIPTION OF THE INVENTION

In one aspect of the invention is a liquid cleansing composition, including but not limited to:
  a. about 5 to 30% by wt. of total synthetic anionic surfactant(s);
  b. about 0.5 to 5% by wt. of total hydrophobically modified acrylate copolymer(s);
  c. about 0.5 to 5% by wt. of total normal C8 to C16 alkyl carboxylic acid(s);
  d. wherein the wt. % ratio range of the total hydrophobically modified acrylate copolymer(s) to the total normal alkyl carboxylic acid(s) is about 0.1 to 3;
  e. wherein the composition has a pH range of about 5 to 10;
  f. wherein the composition contains less than 0.5% by wt. of total oil(s) and waxes selected from hydrocarbons, triglycerides and silicones with a number average particle size under 1000 microns; and
  g. wherein the Standard Delta zero shear viscosity ratio (as defined below) of the liquid cleansing composition is more than 2 in the case of the hydrophobically modified acrylate copolymer(s) effect or more than 30 in the case of the total normal C8 to C16 alkyl carboxylic acid(s) effect.

DETAILED DESCRIPTION OF THE INVENTION

In one aspect of the invention is a liquid cleansing composition, including but not limited to:
  a. about 5 to 30% by wt. of total synthetic anionic surfactant(s);
  b. about 0.5 to 5% by wt. of total hydrophobically modified acrylate copolymer(s);

c. about 0.5 to 5% by wt. of total normal C8 to C16 alkyl carboxylic acid(s); preferably C12 to C16, or more preferably C12 carboxylic acid(s);
d. wherein the wt. % ratio range of the total hydrophobically modified acrylate copolymer(s) to the total normal alkyl carboxylic acid(s) is about 0.1 to 3; preferably about 0.3 to 1;
e. wherein the composition has a pH range of about 5 to 10; (preferably about 6.8 to 10 when at least 90% by wt. of the total normal carboxylic acid(s) is C12 to C16), and more preferably about 6.8 to 7.8 for when at least 90% by wt. of the total normal carboxylic acid(s) is C12 normal carboxylic acid);
f. wherein the composition contains less than 0.5% by wt. of total oil(s) and waxes selected from hydrocarbons, triglycerides and silicones with a number average particle size under 1000 microns (preferably under 500 microns); and
g. wherein the Standard Delta zero shear viscosity ratio of the liquid cleansing composition is more than 2 in the case of the hydrophobically modified acrylate copolymer(s) effect or more than 30 in the case of the total normal C8 to C16 alkyl carboxylic acid(s) effect.

Standard Delta shear viscosity ratio is defined as being equal to N B where A is the shear viscosity at 25 C of an inventive liquid cleansing composition containing both hydrophobically modified acrylate copolymer(s) and normal C8 to C16 alkyl carboxylic acid(s) and B is the shear viscosity at 25 C of an otherwise identical comparative cleansing composition but containing in a first case less than 0.1% by wt. of hydrophobically modified acrylate copolymer(s) ("hydrophobically modified acrylate copolymer(s) effect") or in a second case less than 0.1% by wt. of normal C8 to C16 alkyl carboxylic acid(s) ("total normal C8 to C16 alkyl carboxylic acid(s) effect").

Preferably the total anionic surfactant(s) wt. % is greater than 6, 7 or 8 and less than 20, 15 or 12 wt. %. Preferably total acrylate copolymer(s) wt. % is greater than 0.6, 0.8 or 1 and less than 4, 3 or 2 wt. %. Preferably total C8 to C16 alkyl carboxylic acid(s) wt. % is greater than 1, 1.5 or 2 and less than 5, 4.5 or 4 wt. %. Preferably the wt. % ratio of the total acrylate copolymer(s) to the total alkyl carboxylic acid(s) is greater than 0.1, 0.2 or 0.3 and less than 3, 2 or 1 wt. %.

In a further embodiment the cleansing composition further includes total amphoteric surfactant(s) in the range of 0 to about 5 wt. %. For example the amphoteric surfactant(s) may include one or more surfactants selected from the group consisting of alkyl betaines, alkyl amino betaines, hydroxysultaines, alkyl amphoacetates, and alkylampho carboxyglycinates (preferably alkyl betaines).

Preferably the anionic surfactant(s) includes one or more surfactants selected from the group consisting of alkyl sulfates, alkyl ether sulfates, alkyl sulfonates, alkylbenzene sulfonates, alkyl succinates, alkyl sulfosuccinates, alkyl olefin sulfonates, alkyl sarcosinates, octoxynol phosphates nonoxynol phosphates, alkyl taurates, polyoxyethylene sulfates, polyoxyethylene isethionates, alkyl carboxylates, and alkyl ether carboxylates or blends thereof (more preferably alkyl ether sulfates).

Advantageously the acrylate copolymer(s) includes one or more copolymers containing at least one monomer selected from the group consisting of methacrylic acid, acrylic acid, amino acrylic acid, an acrylic acid ester of a C8-30 alkyl, alkylaryl, aryl, heterocyclic, alkoxyl, alkoxyl alkyl ester of a C8-30 alkyl or alkenyl; either substituted or unsubstituted; a methacrylic acid ester of a C8-C30 alkyl, alkylaryl, aryl, heterocyclic, alkoxyl, alkoxyl alkyl ester of a C8-30 alkyl, or alkenyl; either substituted or unsubstituted; a C1-4 alkyl acrylate, and a C1-4 methacrylate; either substituted or unsubstituted.

In a further embodiment, the cleansing composition includes insoluble component(s) selected from the group consisting of glass beads, plastic beads, hydrophobic organic materials, hydrophobic inorganic materials, crystalline solids, air and gas bubbles. In another embodiment a solid particulate optical modifier with an average diameter of at least about 30 microns may be added to the composition. In addition exfoliant particles greater than about 50 microns in average diameter at a concentration of less than about 10% by wt. may optionally be included. In a preferred embodiment active agent(s) are present in the range of about 0.01 to 50% by wt.

Surfactants:

Anionic surfactants are included in the inventive cleansing composition. Surfactants are compounds that have hydrophobic and hydrophilic portions that act to reduce the surface tension of the aqueous solutions they are dissolved in. Other useful surfactants can include nonionic, amphoteric, and cationic surfactants, and blends thereof.

Synthetic Anionic Surfactants:

The cleansing composition of the present invention contains one or more non-soap or synthetic anionic detergents. Synthetic anionic surfactants are preferably used at levels as low as 5, 6, 7 or 8% by wt. and at levels as high as 12, 15, 20 or 30% by wt. The C8-C18 carboxylic acids in the inventive composition produce soaps in the higher pH range of the inventive composition according to the acid-base equilibria. The composition has a pH range of about 5 to 10 when at least 90% by wt. of the total normal carboxylic acid(s) is C12 to C16. In a further embodiment the composition has a pH range of about 6.8 to 10 when at least 90% by wt. of the total normal carboxylic acid(s) is C12 to C16. In another embodiment the composition has a pH range of about 6.8 to 7.8 when at least 90% by wt. of the total normal carboxylic acid(s) is C12.

The anionic detergent active which may be used in the invention may be aliphatic sulfonates, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or aromatic sulfonates such as alkyl benzene sulfonate. The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$-$C_{22}$ sulfosuccinates); alkyl and acyl taurates, alkyl and acyl sarcosinates, sulfoacetates, $C_8$-$C_{22}$ alkyl phosphates and phosphates, alkyl phosphate esters and alkoxyl alkyl phosphate esters, acyl lactates, $C_8$-$C_{22}$ monoalkyl succinates and maleates, sulphoacetates, alkyl glucosides and acyl isethionates, and the like.

Sulfosuccinates may be monoalkyl sulfosuccinates having the formula:

$$R^4O_2CCH_2CH(SO_3M)CO_2M; \text{ and}$$

amide-MEA sulfosuccinates of the formula;

$$R^4CONHCH_2CH_2O_2CCH_2CH(SO_3M)CO_2M$$

wherein $R^4$ ranges from $C_8$-$C_{22}$ alkyl and M is a solubilizing cation.

Sarcosinates are generally indicated by the formula:

$$R^1 CON(CH_3)CH_2CO_2M,$$

wherein $R^1$ ranges from $C_8$-$C_{20}$ alkyl and M is a solubilizing cation.

Taurates are generally identified by formula:

$$R^2CONR^3CH_2CH_2SO_3M$$

wherein $R^2$ ranges from $C_8$-$C_{20}$ alkyl, $R^3$ ranges from $C_1$-$C_4$ alkyl and M is a solubilizing cation.

The inventive cleansing composition may contain $C_8$-$C_{18}$ acyl isethionates. These esters are prepared by reaction between alkali metal isethionate with mixed aliphatic carboxylic acids having from 6 to 18 carbon atoms and an iodine value of less than 20. At least 75% of the mixed carboxylic acids have from 12 to 18 carbon atoms and up to 25% have from 6 to 10 carbon atoms.

The acyl isethionate may be an alkoxylated isethionate such as is described in Ilardi et al., U.S. Pat. No. 5,393,466, titled "Fatty Acid Esters of Polyalkoxylated isethonic acid; issued Feb. 28, 1995; hereby incorporated by reference. This compound has the general formula:

$$RC-O(O)-C(X)H-C(Y)H_2-(OCH-CH_2)_m-SO_3M^+$$

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

Amphoteric Surfactants

One or more amphoteric surfactants may be used in this invention. Amphoteric surfactants are preferably used at levels as low as 0, 1, or 1.5% by wt. and at levels as high as 3, 5, or 7% by wt. Such surfactants include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

$$R^1-[-C(O)-NH(CH_2)_n-]_m-N^+-(R^2)(R^3)X-Y$$

where $R^1$ is alkyl or alkenyl of 7 to 18 carbon atoms;
$R^2$ and $R^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl, and $$Y \text{ is } -CO_2- \text{ or } -SO_3-$$

Suitable amphoteric surfactants within the above general formula include simple betaines of formula:

$$R^1-N^+-(R^2)(R^3)CH_2CO_2^-$$

and amido betaines of formula:

$$R^1-CONH(CH_2)_n-N^+-(R^2)(R^3)CH_2CO_2^-$$

where n is 2 or 3.

In both formulae $R^1$, $R^2$ and $R^3$ are as defined previously. $R^1$ may in particular be a mixture of $C_{12}$ and $C_{14}$ alkyl groups derived from coconut oil so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

$$R^1-N^+-(R^2)(R^3)(CH_2)_3SO_3^-$$

Or $$R^1-CONH(CH_2)_m-N^+-(R^2)(R^3)(CH_2)_3SO_3^-$$

where m is 2 or 3, or variants of these in which $-(CH_2)_3SO_3^-$ is replaced by $$-CH_2C(OH)(H)CH_2SO_3^-$$

In these formulae $R^1$, $R^2$ and $R^3$ are as discussed previously.

Amphoacetates and diamphoacetates are also intended to be covered in possible zwitterionic and/or amphoteric compounds which may be used such as e.g., sodium lauroamphoacetate, sodium cocoamphoacetate, and blends thereof, and the like.

Nonionic Surfactants

One or more nonionic surfactants may be used in the cleansing composition of the present invention. Nonionic surfactants are preferably used at levels as low as 0, 1, or 1.5% by wt. and at levels as high as 3, 5, or 7% by wt. The nonionics which may be used include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$-$C_{22}$) phenols ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxide, and the like.

Preferred nonionic surfactants include carboxylic acid/alcohol ethoxylates having the following structures
a) HOCH2(CH2)n(CH2CH2O)xH or
b) HOOC(CH2)m(CH2CH2O)yH;
where m, n are independently <18; and x, y are independently >1. preferably m, n are independently 6 to 18; x, y are independently 1 to 30;
c) HOOC(CH2)i-CH=CH-(CH2)k(CH2CH2O)zH;
where i, k are independently 5 to 15; and z is independently 5 to 50. preferably i, k are independently 6 to 12; and z is independently 15 to 35.

The nonionic may also include a sugar amide, such as a polysaccharide amide. Specifically, the surfactant may be one of the lactobionamides described in U.S. Pat. No. 5,389,279 to Au et al. titled "Compositions Comprising Nonionic Glycolipid Surfactants issued Feb. 14, 1995; which is hereby incorporated by reference or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991; hereby incorporated into the subject application by reference.

Normal Carboxylic Acids

Normal alkyl carboxylic acids selected from C8-C16 alkyl range are used in the invention. Preferably carboxylic acid(s), such as lauric (C12), myristic (C14) or palmitic (C16) acids are used alone or in combination. Advantageously the carboxylic acid(s) are used at levels as low as 1.0, 1.5, or 2% by wt. and at levels as high as 4, 4.5 or 5% by wt. where a portion may exist as the corresponding soap(s) depending on the pH and the specific pKa of the carboxylic acid(s) in question.

Hydrophobically modified, crosslinked, anionic acrylic copolymers

Hydrophobically modified, crosslinked, anionic acrylic copolymer(s) are used for the invention and are typically in the form of random polymers, but may also exist in other forms such as block, star, graft, and the like and blends thereof. In one embodiment, the hydrophobically modified, crosslinked, anionic acrylic copolymer may be synthesized from at least one acidic monomer and at least one hydrophobic ethylenically unsaturated monomer. Examples of suitable acidic monomers include those ethylenically unsaturated acid monomers that may be neutralized by a base. Examples of suitable hydrophobic ethylenically unsaturated monomers include those that contain a hydrophobic chain having a carbon chain length of at least 3 carbon atoms. Advantageously the acrylic copolymer(s) are used at levels as low as 0.5, 0.8, or 1% by wt. and at levels as high as 2, 3 or 4% by wt. of total copolymer(s) and may consist of one or a blend of copolymers.

In another embodiment, the hydrophobically modified, crosslinked, anionic acrylic copolymer includes those compositions derived from at least one unsaturated carboxylic acid monomer; at least one hydrophobic monomer; a hydrophobic chain transfer agent comprising alkyl mercaptans, thioesters, amino acid-mercaptan-containing compounds or peptide fragments, or combinations thereof; a cross-linking agent; and, optionally, a steric stabilizer; wherein the amount of said unsaturated carboxylic acid monomer is from about 60 percent to about 98 percent by weight based upon the total weight of said unsaturated monomers and said hydrophobic monomer, as set forth in U.S. Pat. No. 6,433,061 incorporated herein by reference. Suitable agents include acrylate containing homo and copolymers such as the crosslinked poly acrylates available under the CARBOPOL trade name, the hydrophobically modified cross linked polyacrylates available under the AQUA trade name, and the PEMULEN trade name (all sold by Lubrizol Company, Wickliffe, Ohio), the alkali swellable acrylic latex polymers sold by Rohm and Haas (Philadelphia, Pa.) under the ACUSOL or ACULYN trade names and Synthalen 400 (available from 3V located in Hackensack, N.J.).

Cationic Skin Conditioning Agents

A useful component in compositions according to the invention is a cationic skin feel agent or polymer, such as for example cationic celluloses. Cationic polymers are preferably used at levels as low as about 0.1 to 2% up to levels as high as the solubility limit of the specific polymer, or preferably up to about 4 to 5% by wt., provided that the solubility limit of the particular cationic polymer or blend thereof is not exceeded.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10 . Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

A particularly suitable type of cationic polysaccharide polymer that can be used is a cationic guar gum derivative, such as guar hydroxypropyltrimonium chloride (Commercially available from Rhone-Poulenc in their JAGUAR trademark series). Examples are JAGUAR C13S, which has a low degree of substitution of the cationic groups and high viscosity, JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Particularly preferred cationic polymers are JAGUAR C13S, JAGUAR C15, JAGUAR C17 and JAGUAR C16 and JAGUAR C162, especially JAGUAR C13S, and JAGUAR C-14/BFG. The JAGUAR C14/BFG material is the same molecule as JAGUAR C13, except that a glyoxal cross linker has replaced the boron. Other cationic skin feel agents known in the art may be used provided that they are compatible with the inventive formulation.

Other suitable examples of surfactants described above which may be used are described in "Surface Active Agents and Detergents" (Vol. I & II) by Schwartz, Perry & Berch, incorporated into the subject application by reference in its entirety.

In addition, the inventive cleansing composition of the invention may include 0 to 15% by wt. optional ingredients as follows: perfumes; sequestering agents, such as tetrasodium ethylenediaminetetraacetate (EDTA), EHDP or mixtures in an amount of 0.01 to 1%, preferably 0.01 to 0.05%; and soluble coloring agents, and the like; all of which are useful in enhancing the appearance or cosmetic properties of the product.

The compositions may further comprise antimicrobials such as 2-hydroxy-4,2', 4' trichlorodiphenylether (DP300); preservatives such as methylisothiazolinone/methylchloroisothiazolinone (Kathon, MIT), dimethyloldimethylhydantoin/iodopropynyl butylcarbamate (Glydant XL1000,), parabens, sorbic acid etc., and the like.

The compositions may also comprise coconut acyl mono- or diethanol amides as suds boosters, and strongly ionizing salts such as sodium chloride and sodium sulfate may also be used to advantage for increasing viscosity. Preferably strongly ionizing salts, otherwise known as electrolytes, will be present at less than 5, 4, 3, or 1% by wt.

Antioxidants such as, for example, butylated hydroxytoluene (BHT) and the like may be used advantageously in amounts of about 0.01% or higher if appropriate.

Emollients

The term "emollient" is defined as a substance which softens or improves the elasticity, appearance, and youthfulness of the skin (stratum corneum) by either increasing its water content, adding, or replacing lipids and other skin nutrients; or both, and keeps it soft by retarding the decrease of its water content.

Moisturizers that also are Humectants such as polyhydric alcohols, e.g. glycerin and propylene glycol, and the like; and polyols such as the polyethylene glycols including Polyox WSR N-60K (PEG-45M) and the like are used in a preferred embodiment of the invention. Humectants are preferably used at levels as low as 0.5, 1, 3 or 5% by wt. and at levels as high as 6, 8 or 10% by wt. Advantageously polyethylene glycols comprise at least 0.025, 0.05, or 0.1% by wt. of the inventive composition.

Hydrophobic emollients with weight average particle sizes below either 1000 or 500 microns in diameter are defined herein as "finely dispersed oils" and are in another embodiment present at total levels of less than about 0.5, 0.4, 0.3, 0.2 or 0.1% by wt. in the inventive composition and may be absent from the composition. These hydrophobic emollients include but are not limited to the following:

(a) silicone oils and modifications thereof such as linear and cyclic polydimethylsiloxanes; amino, alkyl, alkylaryl, and aryl silicone oils;

(b) fats and oils including natural fats and oils (triglycerides) such as jojoba, soybean, sunflower, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin, and derivatives thereof;

(d) hydrophobic plant extracts;

(e) hydrocarbons such as petrolatum, polybutene, liquid paraffins, microcrystalline wax, ceresin, squalene, pristan and mineral oil;

(f) higher alcohols such as lauryl, cetyl, stearyl, oleyl, behenyl, cholesterol and 2-hexydecanol alcohol;

(g) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(h) essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils;

(i) mixtures of any of the foregoing components, and the like.

Isotropic Micellar Phase Compositions:

The inventive cleansing composition possesses substantially isotropic micellar phase microstructure but may have low levels of lamellar phase structure at the lower level of the operative pH range in addition to isotropic micellar phase.

The rheological behavior of all surfactant solutions, including liquid cleansing solutions, is strongly dependent on the microstructure, i.e., the shape and concentration of micelles or other self-assembled structures in solution.

When there is sufficient surfactant to form micelles (concentrations above the critical micelle concentration or CMC), for example, spherical, cylindrical (rod-like or discoidal), spherocylindrical, or ellipsoidal micelles may form. As surfactant concentration increases, ordered liquid crystalline phases such as lamellar phase, hexagonal phase, cubic phase or L3 sponge phase may form. The non-isotropic hexagonal phase consists of long cylindrical micelles arranged in a hexagonal lattice. In general, the microstructure of most personal care products consists of either an isotropic dispersion including spherical micelles; and rod micelles; or an ordered liquid crystalline phase such as a lamellar dispersion.

As noted above, micelles may be spherical or rod-like.

Formulations having spherical micelles tend to have a low viscosity and exhibit Newtonian shear behavior (i.e., viscosity stays constant as a function of shear rate; thus, if easy pouring of product is desired, the solution is less viscous. In these systems, the viscosity increases linearly with surfactant concentration.

Rod micellar solutions are more viscous because movement of the longer micelles is restricted. At a critical shear rate, the micelles align and the solution becomes shear thinning. Addition of salts increases the size of the rod micelles thereof increasing zero shear viscosity (i.e., viscosity when sitting in bottle) which helps suspend particles but also increases critical shear rate (point at which product becomes shear thinning; higher critical shear rates means that the product is more difficult to pour).

Lamellar and other liquid crystalline dispersions may be present at the lower end of the operative pH range as discussed above. Such dispersions differ from both spherical and rod-like micelles because they can have high zero shear viscosity (because of the close packed arrangement of constituent lamellar droplets), yet these solutions are very shear thinning (readily dispense on pouring). That is, the solutions can become thinner than rod micellar solutions at moderate shear rates.

One way of characterizing isotropic micellar dispersions (hereinafter "isotropic compositions") include Brookfield viscosity measurement as described below. The inventive substantially isotropic composition has e.g. a viscosity in the range of about 100 to about 50000 mPas@ 20 rpm at 25 C as measured by a Brookfield RVT rheometer with Spindle 5. In another embodiment, the viscosity is in the range of about 1000 to 25000 mPas at 25 C.

Optional active agents

Advantageously, active agents other than conditioning agents such as emollients or moisturizers defined above may be added to the cleansing composition in a safe and effective amount during formulation to treat the skin during the use of the product . Suitable active ingredients include those that are water soluble or are dispersible within the limits provided above. Suitable active agents may be advantageously selected from antimicrobial and antifungal actives, vitamins, anti-acne actives; anti-wrinkle, anti-skin atrophy and skin repair actives; skin barrier repair actives; non- steroidal cosmetic soothing actives; artificial tanning agents and accelerators; skin lightening actives; sunscreen actives; sebum stimulators; sebum inhibitors; anti-oxidants; protease inhibitors; skin tightening agents; anti-itch ingredients; hair growth inhibitors; 5-alpha reductase inhibitors; desquamating enzyme enhancers; anti-glycation agents; topical anesthetics, or mixtures thereof; and the like.

These active agents may be selected from water soluble active agents, oil soluble active agents, pharmaceutically-acceptable salts and mixtures thereof. Advantageously the agents will be soluble or dispersible in the cleansing composition. The term "active agent" as used herein, means personal care actives which can be used to deliver a benefit to the skin and/or hair and which generally are not used to confer a conditioning benefit, as is conferred by humectants and emollients previously described herein. The term "safe and effective amount" as used herein, means an amount of active agent high enough to modify the condition to be treated or to deliver the desired skin care benefit, but low enough to avoid serious side effects. The term "benefit," as used herein, means the therapeutic, prophylactic, and/or chronic benefits associated with treating a particular condition with one or more of the active agents described herein. What is a safe and effective amount of the active agent ingredient will vary with the specific active agent, the ability of the active to penetrate through the skin, the age, health condition, and skin condition of the user, and other like factors. Preferably the composition of the present invention comprise from about 0.01% to about 50%, more preferably from about 0.05% to about 25%, even more preferably 0.1% to about 10%, and most preferably 0.1% % to about 5%, by weight of the active agent component.

Anti-acne actives can be effective in treating acne vulgaris, a chronic disorder of the pilosebaceous follicles. Nonlimiting examples of useful anti-acne actives include the keratolytics such as salicylic acid (o-hydroxybenzoic acid), derivatives of salicylic acid such as 5-octanoyl salicylic acid and 4 methoxysalicylic acid, and resorcinol; retinoids such as retinoic acid and its derivatives (e.g., cis and trans); sulfur-containing D and L amino acids and their derivatives and salts, particularly their N-acetyl derivatives, mixtures thereof and the like.

Antimicrobial and antifungal actives can be effective to prevent the proliferation and growth of bacteria and fungi. Nonlimiting examples of antimicrobial and antifungal actives include b-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, triclosan; triclocarban; and mixtures thereof and the like.

Anti-wrinkle, anti-skin atrophy and skin repair actives can be effective in replenishing or rejuvenating the epidermal layer. These actives generally provide these desirable skin care benefits by promoting or maintaining the natural process of desquamation. Nonlimiting examples of antiwrinkle and anti-skin atrophy actives include vitamins, minerals, and skin nutrients such as milk, vitamins A, E, and K; vitamin alkyl esters, including vitamin C alkyl esters; magnesium, calcium, copper, zinc and other metallic components; retinoic acid and its derivatives (e.g., cis and trans); retinal; retinol; retinyl esters such as retinyl acetate, retinyl palmitate, and retinyl propionate; vitamin B 3 compounds (such as niacinamide and nicotinic acid), alpha hydroxy acids, beta hydroxy acids, e.g. salicylic acid and derivatives thereof (such as 5-octanoyl salicylic acid, heptyloxy 4 salicylic acid, and 4-methoxy salicylic acid); mixtures thereof and the like.

Skin barrier repair actives are those skin care actives which can help repair and replenish the natural moisture barrier function of the epidermis. Nonlimiting examples of skin barrier repair actives include lipids such as cholesterol, ceramides, sucrose esters and pseudo-ceramides as described in European Patent Specification No. 556,957; ascorbic acid; biotin; biotin esters; phospholipids, mixtures thereof, and the like.

Non-steroidal cosmetic soothing actives can be effective in preventing or treating inflammation of the skin. The soothing active enhances the skin appearance benefits of the present invention, e.g., such agents contribute to a more uniform and acceptable skin tone or color. Nonlimiting examples of cosmetic soothing agents include the following categories: propionic acid derivatives; acetic acid derivatives; fenamic acid derivatives; mixtures thereof and the like. Many of these cosmetic soothing actives are described in U.S. Pat. No. 4,985,459 to Sunshine et al., issued Jan. 15, 1991, incorporated by reference herein in its entirety. Artificial tanning actives can help in simulating a natural suntan by increasing melanin in the skin or by producing the appearance of increased melanin in the skin. Nonlimiting examples of artificial tanning agents and accelerators include dihydroxyacetaone; tyrosine; tyrosine esters such as ethyl tyrosinate and glucose tyrosinate; mixtures thereof, and the like.

Skin lightening actives can actually decrease the amount of melanin in the skin or provide such an effect by other mechanisms. Nonlimiting examples of skin lightening actives useful herein include aloe extract, alpha-glyceryl-L-ascorbic acid, aminotyroxine, ammonium lactate, glycolic acid, hydroquinone, 4 hydroxyanisole, mixtures thereof, and the like.

Also useful herein are sunscreen actives. A wide variety of sunscreen agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of Cosmetics Science and Technology, all of which are incorporated herein by reference in their entirety. Nonlimiting examples of sunscreens which are useful in the compositions of the present invention are those selected from the group consisting of octyl methoxyl cinnamate (Parsol MCX) and butyl methoxy benzoylmethane (Parsol 1789), 2-ethylhexyl p-methoxycinnamate, 2-ethylhexyl N,N-dimethyl-p-aminobenzoate, p-aminobenzoic acid, 2-phenylbenzimidazole-5-sulfonic acid, oxybenzone, mixtures thereof, and the like.

Sebum stimulators can increase the production of sebum by the sebaceous glands. Nonlimiting examples of sebum stimulating actives include bryonolic acid, dehydroetiandrosterone (DHEA), orizanol, mixtures thereof, and the like.

Sebum inhibitors can decrease the production of sebum by the sebaceous glands. Nonlimiting examples of useful sebum inhibiting actives include aluminum hydroxy chloride, corticosteroids, dehydroacetic acid and its salts, dichlorophenyl imidazoldioxolan (available from Elubiol), mixtures thereof, and the like.

Also useful as actives in the present invention are protease inhibitors. Protease inhibitors can be divided into two general classes: the proteinases and the peptidases. Proteinases act on specific interior peptide bonds of proteins and peptidases act on peptide bonds adjacent to a free amino or carboxyl group on the end of a protein and thus cleave the protein from the outside. The protease inhibitors suitable for use in the present invention include, but are not limited to, proteinases such as serine proteases, metalloproteases, cysteine proteases, and aspartyl protease, and peptidases, such as carboxypepidases, dipeptidases and aminopepidases, mixtures thereof and the like.

Other useful as active ingredients in the present invention are skin tightening agents. Nonlimiting examples of skin tightening agents which are useful in the compositions of the present invention include monomers which can bind a polymer to the skin such as terpolymers of vinylpyrrolidone, (meth)acrylic acid and a hydrophobic monomer comprised of long chain alkyl (meth)acrylates, mixtures thereof, and the like.

Active ingredients in the present invention may also include anti-itch ingredients. Suitable examples of anti-itch ingredients which are useful in the compositions of the present invention include hydrocortisone, methdilizine and trimeprazineare, mixtures thereof, and the like.

Nonlimiting examples of hair growth inhibitors which are useful in the compositions of the present invention include 17 beta estradiol, anti angiogenic steroids, curcuma extract, cycloxygenase inhibitors, evening primrose oil, linoleic acid and the like. Suitable 5-alpha reductase inhibitors such as ethynylestradiol and, genistine mixtures thereof, and the like.

Nonlimiting examples of desquamating enzyme enhancers which are useful in the compositions of the present invention include alanine, aspartic acid, N methyl serine, serine, trimethyl glycine, mixtures thereof, and the like.

A nonlimiting example of an anti-glycation agent which is useful in the compositions of the present invention would be Amadorine (available from Barnet Products Distributor), and the like.

Solid particulate optical modifiers

An useful optional component of compositions according to the present invention is that of solid particulate optical modifiers, preferably light reflecting platelet shaped or platy particles. These particles will preferably have an average particle size $D_{50}$ ranging from about 25,000 to about 150,000 nm. For plate-like materials the average particle size is a number average value. The platelets are assumed to have a circular shape with the diameter of the circular surface averaged over many particles. The thickness of the plate-like particles is considered to be a separate parameter. For instance, the platelets can have an average particle size of 35,000 nm and an average thickness of 400 nm. For purposes herein, thickness is considered to range from about 100 to about 600 nm. Laser light scattering can be utilized for measurement except that light scattered data has to be mathematically corrected from the spherical to the non-spherical shape. Optical and electron microscopy may be used to determine average particle size. Thickness is normally only determined via optical or electron microscopy.

The refractive index of these particles may be at least about 1.8, generally from about 1.9 to about 4, e.g. from about 2 to about 3, and between about 2.5 and 2.8.

Illustrative but not limiting examples of light reflecting particles are bismuth oxychloride (single crystal platelets) and titanium dioxide and/or iron oxide coated mica. Suitable bismuth oxychloride crystals are available from EM Industries, Inc. under the trademarks Biron® NLY-L-2X CO and Biron® Silver CO (wherein the platelets are dispersed in castor oil); Biron® Liquid Silver (wherein the particles are dispersed in a stearate ester); and Nailsyn® IGO, Nailsyn® II C2X and Nailsyn® II Platinum 25 (wherein the platelets are dispersed in nitrocellulose). Most preferred is a system where bismuth oxychloride is dispersed in a $C_2$- $C_{40}$ alkyl ester such as in Biron® Liquid Silver.

Among the suitable titanium dioxide coated mica platelets are materials available from EM Industries, Inc. These include Timiron® MP-45 (particle size range 49,000-57,000 nm), Timiron® MP-99 (particle size range 47,000-57,000 nm), Timiron® MP-47 (particle size range 28,000-38,000 nm), Timiron® MP-149 (particle size range 65,000-82,000 nm), and Timiron® MP-18 (particle size range 41,000-51,000 nm). The weight ratio of titanium dioxide coating to the mica platelet may range from about 1:10 to about 5:1, preferably from about 1:6 to about 1:7, by weight. Advantageously the compositions will generally be substantially free of titanium dioxide outside of that required for coating mica.

Among the suitable iron oxide and titanium dioxide coated mica platelets are materials available from EM Industires, Inc. These include Timiron® MP-28 (particle size range 27,000-37,000 nm), Timiron® MP-29 (particle size range 47,000-55,000 nm), and Timiron® MP-24 (particle size range 56,000-70,000 nm).

Among the suitable iron oxide coated mica platelets are materials available from EM Industires, Inc. These include Colorona® Bronze Sparkle (particle size range 28,000-42,000 nm), Colorona® Glitter Bronze (particle size range 65,000-82,000 nm), Colorona® Copper Sparkle (particle size range 25,000-39,000 nm), and Colorona® Glitter Copper (particle size range 65,000-82,000 nm).

Suitable coatings for mica other than titanium dioxide and iron oxide may also achieve the appropriate optical properties required for the present invention. These types of coated micas must also meet the refractive index of at least about 1.8. Other coatings include silica on the mica platelets.

Advantageously the solid particulate optical modifier has an average diameter of at least about 30 microns. In a further embodiment the solid particulate optical modifier is present in a minimum concentration of at least about 0.2% by wt.

Exfoliants

The inventive composition may contain particles that are greater than 50 microns in average diameter that help remove dry skin. Advantageously they are present at a concentration of less than about 10% by wt.

Not being bound by theory, the degree of exfoliation depends on the size and morphology of the particles. Large and rough particles are usually very harsh and irritating. Very small particles may not serve as effective exfoliants. Such exfoliants used in the art include natural minerals such as silica, talc, calcite, pumice, tricalcium phosphate; seeds such as rice, apricot seeds, etc; crushed shells such as almond and walnut shells; oatmeal; polymers such as polyethylene and polypropylene beads, flower petals and leaves; microcrystalline wax beads; jojoba ester beads, and the like. These exfoliants come in a variety of particle sizes and morphology ranging from micron sized to a few mm. They also have a range of hardness. Some examples are given in table 1 below.

TABLE A

| Material | Hardness (Mohs) |
| --- | --- |
| Talc | 1 |
| Calcite | 3 |
| Pumice | 4-6 |
| Walnut Shells | 3-4 |
| Dolomite | 4 |
| Polyethylene | ~1 |

The invention will now be described in greater detail by way of the following non-limiting examples. The examples are for illustrative purposes only and not intended to limit the invention in any way. Physical test methods are described below:

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

All percentages in the specification and examples are intended to be by weight unless stated otherwise.

EXAMPLE 1

The individual and combined effects on relative zero shear viscosity of lauric (C12) acid and Aqua SF-1, a hydrophobically modified cross-linked acrylate, were studied in the pH range of 6.88 to 8.59 for the inventive and comparative formulations described in Table 1. Inventive composition A was found to have substantially higher relative zero shear viscosity compared to the sum of the viscosities of comparative compositions B and C separately containing the same levels of acid and acrylate within the same narrow pH range. The log of viscosity vs. pH for compositions A, B and C is plotted in FIG. 1 and listed in Table 2.

TABLE 1

Viscosity study of inventive composition
A vs. comparative compositions B and C.

| | % by wt. | | |
|---|---|---|---|
| INCI NAME OF MATERIAL | Sample A | Sample B | Sample C |
| DI Water and miscellaneous | 61.23 | 64.23 | 63.03 |
| Acrylates copolymer | 1.8 | 1.8 | — |
| Titanium Dioxide | 0.05 | 0.05 | 0.05 |
| Sodium Laureth Sulfate | 10.32 | 10.32 | 10.32 |
| Lauric acid | 3 | — | 3 |
| PEG 45M | 0.05 | 0.05 | 0.05 |
| Glycerin | 1.5 | 1.5 | 1.5 |
| Tetrasodium EDTA | 0.05 | 0.05 | 0.05 |
| Sodium Hydroxide | 0.5 | 0.5 | 0.5 |
| Quench water | 20 | 20 | 20 |
| Methylchloroisothiazolinone and Methylisothiazolinone | 0.0003 | 0.0003 | 0.0003 |
| Fragrance | 1 | 1 | 1 |
| Sodium Chloride | 0.5 | 0.5 | 0.5 |
| Acrylates to Carboxylic Acids ratio | 0.6 | — | — |
| TOTAL | 100 | 100 | 100 |

Preparation method for samples A, B and C.
Add water
Add acrylates polymer (if required)
Start heating to 60 C
Add titanium dioxide
Add sodium laureth sulfate
Add lauric acid (if required)
Mix at 60 C until uniform
Premix PEG 45M in glycerin until evenly dispersed
Add PEG 45M/glycerin submix
Add tetrasodium EDTA
Adjust pH to 6.9 with sodium hydroxide
Turn off heat and start cooling
Add quench water
Add preservative under 45 C
Add fragrance under 40 C
Add sodium chloride
Split batch in half and add sodium hydroxide to one portion until pH is at 8.6 Mix different ratios of high pH portion with low pH portion to get samples at varying pH.

TABLE 2

Figure 1:
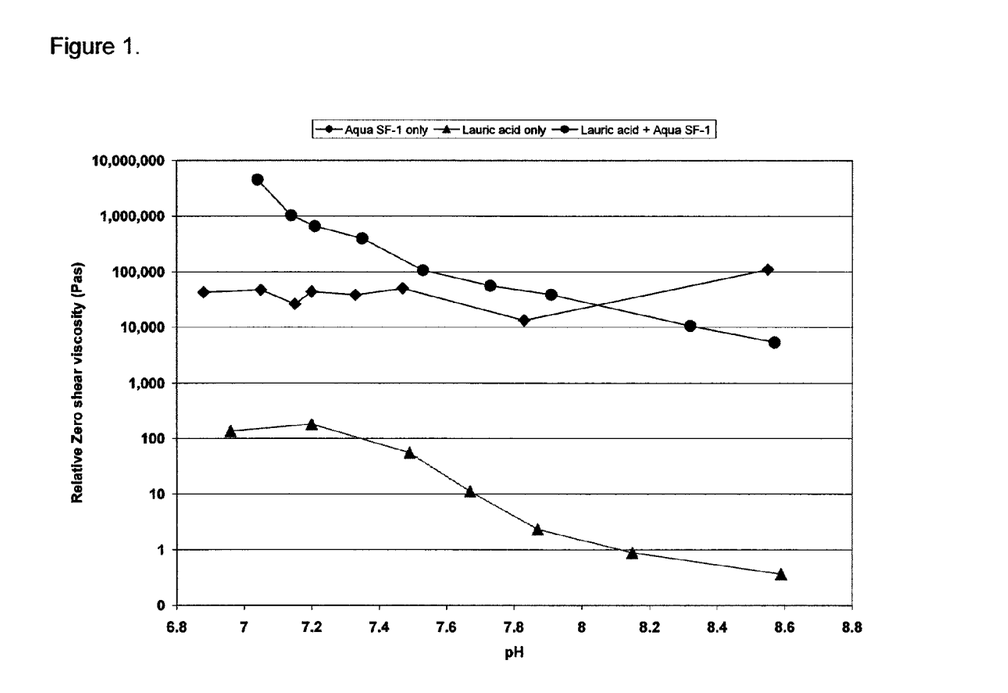
FIG. 1 is a graphical log-linear representation displaying relative zero shear viscosity (Pas) as a function of pH for inventive and comparative compositions described in Example 1.

Viscosity properties versus pH results for samples
A, B and C described in Table 1 and graphically depicted
in FIG. 1. Rheological measurements were performed
according to the procedure described below.

| # | pH | Pas |
|---|---|---|
| | Sample A | |
| 1 | 7.04 | 4497362 |
| 2 | 7.14 | 1022093 |
| 3 | 7.21 | 653597.6 |
| 4 | 7.35 | 396808.5 |
| 5 | 7.53 | 106230 |
| 6 | 7.73 | 55932.52 |
| 7 | 7.91 | 38627.83 |
| 8 | 8.32 | 10564.7 |
| 9 | 8.57 | 5381.425 |
| | Sample B | |
| 1 | 6.88 | 42507.12 |
| 2 | 7.05 | 47215.19 |
| 3 | 7.15 | 26129.6 |
| 4 | 7.2 | 43657.64 |
| 5 | 7.33 | 38061.22 |
| 6 | 7.47 | 49983.25 |
| 7 | 7.83 | 13282.88 |
| 8 | 8.55 | 109358.1 |
| | Sample C | |
| 1 | 6.96 | 135.9763 |
| 2 | 7.2 | 181.288 |
| 3 | 7.49 | 55.31047 |
| 4 | 7.67 | 11.2033 |
| 5 | 7.87 | 2.322179 |
| 6 | 8.15 | 0.890082 |
| 7 | 8.59 | 0.363017 |

Note:
500 gap, 20 min max time (see rheology method procedure below)

EXAMPLE 2

Additional examples of inventive (D and E) and comparative compositions (F, G and H) were prepared as indicated in Table 3 with varying levels of acrylate polymer, with and without salt and the viscosity of the compositions were studied as a function of pH. Synergistic effects on viscosity were observed for the inventive compositions in the inventive pH range compared to comparative cases.

TABLE 3

Additional inventive and comparative examples

| INCI Name of Component | % by wt. | | | | |
|---|---|---|---|---|---|
| | D | E | F | G | H |
| DI Water | 61.65 | 62.04 | 61.48 | 61.83 | 62.03 |
| Acrylates Copolymer | 1.8 | 1.2 | 1.2 | — | — |
| Sodium Laureth Sulfate | 9.0 | 9.0 | 10.3 | 10.3 | 9.0 |
| Cocamide MEA | 1.15 | 1.15 | — | — | 1.15 |
| Lauric acid | 3 | 3 | 3 | 3 | 3 |
| PEG 45M | 0.05 | 0.05 | 0.05 | 0.05 | 0.05 |
| Glycerin | 0.5 | 0.5 | 0.5 | 1.5 | 1.5 |
| Tetrasodium EDTA | 0.05 | 0.05 | 0.05 | 0.05 | 0.05 |
| Sodium Hydroxide | To pH 7.2 | To pH 7.2 | To pH 7.2 | To pH 7.2 | To pH 7.2 |
| Cocamidopropyl betaine | 1.7 | 1.7 | — | — | 1.7 |
| Quench water | 20 | 20 | 20 | 20 | 20 |
| Methylchloroisothiazolinone and methylisothiazolinone | 0.0003 | 0.0003 | 0.0003 | 0.0003 | 0.0003 |
| Fragrance | 0.57 | 0.85 | 0.85 | 0.85 | 0.85 |
| Sodium Chloride | — | — | 0.6 | 1.9 | — |
| Acrylate to Acid ratio | 0.6 | 0.4 | 0.4 | — | — |
| Water and miscellaneous | Qs 100 | Qs 100 | Qs 100 | Qs 100 | Qs 100 |

Notes for examples 1 and 2:
(1) Acrylates Copolymer (Aqua SF-1, Lubrizol, Wickliffe, Ohio)
(2) Sodium Laureth Sulfate (Steol CS170, Stepan, Northfield, Illinois)
(3) Cocamide MEA (Mackamide MEA, McIntyre Group, University Park, Illinois)
(4) Lauric Acid (Prifrac 2922, Uniqema)
(5) PEG 45M (Polyox WSR N60K, Amerchol)
(6) Cocamidopropyl betaine (Tegobetaine F, Goldschmidt)
(7) Methylchloroisothiazolinone and methylisothiazolinone (Kathon CG, Rohm and Haas)

Preparation of Samples D, E, F, G, and H
Add water
Add acrylates polymer (if required)
Start heating to 60 C
Add sodium laureth sulfate
Add cocamide MEA (if required)
Add lauric acid (if required)
Mix at 60 C until uniform
Premix PEG 45M in glycerin until evenly dispersed
Add PEG 45M/glycerin submix
Add tetrasodium EDTA
Adjust pH to 7.2 with sodium hydroxide
Turn off heat and start cooling
Add betaine (if required)
Add quench water
Add preservative under 45 C
Add fragrance under 40 C
Add sodium chloride (if required)
Split batch in half and add sodium hydroxide to one portion until pH is at 8.2 Mix different ratios of high pH portion with low pH portion to get samples at varying pH.

TABLE 4

Rheology data for samples D to H described in Table 3.

Sample D

| pH | 8.54 | 8.2 | 8 | 7.82 | 7.62 | 7.34 |
|---|---|---|---|---|---|---|
| zero shear (Pas) | 52.58 | 490.39 | 1532.61 | 2388.16 | 21253.56 | 79435.64 |

Sample E

| pH | 8.24 | 8.03 | 7.85 | 7.69 | 7.51 | |
|---|---|---|---|---|---|---|
| zero shear (Pas) | 6.97 | 16.55 | 41.19 | 249.50 | 6897.83 | |

Sample F

| pH | 7.24 | 7.49 | 7.62 | 7.83 | 7.98 | |
|---|---|---|---|---|---|---|
| zero shear (Pas) | 9943.35 | 1079.01 | 629.74 | 37.96 | 10.86 | |

Sample G

| pH | 6.86 | 7.28 | 7.55 | 7.77 | 8.25 | |
|---|---|---|---|---|---|---|
| zero shear (Pas) | 1509.357613 | 596.9790937 | 220.6284658 | 22.54627881 | 12.69787234 | |

Sample H

| pH | 7.26 | 7.49 | 7.65 | 7.86 | 8.17 | |
|---|---|---|---|---|---|---|
| zero shear (Pas) | 167.3583847 | 138.9522701 | 8.616806237 | 4.524639879 | 2.782284382 | |

EXAMPLE 3

Inventive compositions with the compositional parameters illustrated in Table 5 may be prepared according to the above procedures to illustrate the synergistic effects on viscosity of specific acrylate polymers, and carboxylic acids using various synthetic anionic surfactants.

TABLE 5

| Anionic Surfactant (Wt. %) | Normal Carboxylic Acid (Wt. %) | Acrylates Copolymer (Wt. %) | pH | Ratio of acrylate polymer to carboxylic acid |
|---|---|---|---|---|
| Ammonium Laureth Sulfate (5) | C12 carboxylic acid (1) | Aqua SF-1 (2) | 6.8 | 2.00 |
| Ammonium Laureth Sulfate (10) | C12 carboxylic acid (3) | Aqua SF-1 (2.5) | 7.4 | 0.83 |
| Ammonium Laureth Sulfate (20) | C12 carboxylic acid (5) | Aqua SF-1 (1.5) | 7.8 | 0.30 |
| Sodium Laureth Sulfate (5) | C16 Carboxylic acid (1) | Acusol 33 (3) | 9 | 3.00 |
| Sodium Laureth Sulfate (10) | C16 Carboxylic acid Acid (3) | Acusol 33 (2.5) | 9.5 | 0.83 |
| Sodium Laureth Sulfate (20) | C16 Carboxylic acid (5) | Acusol 33 (5) | 10 | 1.00 |
| Sodium Lauroyl Sarcosinate (5) | C8 Carboxylic Acid (1) | Acusol 38 (1) | 5 | 1.00 |
| Sodium Lauroyl Sarcosinate (10) | C8 Carboxylic Acid (3) | Acusol 38 (2.5) | 5.5 | 0.83 |
| Sodium Lauroyl Sarcosinate (20) | C8 Carboxylic Acid (5) | Acusol 38 (0.5) | 6 | 0.10 |
| Sodium Lauroyl Sulfosuccinate (5) | C10 Carboxylic Acid (1) | Synthalen 400 (0.5) | 6 | 0.50 |
| Sodium Lauroyl Sulfosuccinate (10) | C10 Carboxylic Acid (3) | Synthalen 400 (4) | 6.5 | 1.33 |
| Sodium Lauroyl Sulfosuccinate (20) | C10 Carboxylic Acid (5) | Synthalen 400 (4) | 7 | 0.80 |
| Sodium Glycinate | C14 Carboxylic | Aqua SF-1 (0.8) | 8 | 0.80 |

TABLE 5-continued

| Anionic Surfactant (Wt. %) | Normal Carboxylic Acid (Wt. %) | Acrylates Copolymer (Wt. %) | pH | Ratio of acrylate polymer to carboxylic acid |
|---|---|---|---|---|
| Sodium Glycinate (10) | Acid (1) C14 Carboxylic Acid (3) | Aqua SF-1 (2) | 8.5 | 0.67 |
| Sodium Glycinate (20) | C14 Carboxylic Acid (5) | Aqua SF-1 (1) | 9 | 0.20 |

Methods:

A) Rheology Method

The following method was used to determine the viscosity for Examples 1 and 2.
Creep Procedure @ 25 C
Conditioning Step
1 min equilibration
Retardation
shear stress (Pa 0.05968)
max step time=20 min
terminate on equilibrium 5%
tolerance, 15 second sample
period
Post Experiment Step
(auto save file)
Geometry
60 mm parallel plate
500 mico m gap distance
Rheometer Details
Texas Instruments AR 500
Rheometer Open graph after running the above procedure on the Rheology Advantage Data Analysis program and select linear region towards end of the graph, near the last points. Using the red divider lines, define region of analysis on the graph. Select the "Straight line function" and run. Once this has been completed a set of values will show up on the graph. Extract the slope value from this data. The zero shear viscosity is determined by dividing the stress (0.05968 Pa) over the slope of the line.

Zero shear (PaS)=[Stress (Pa)]/[Slope (1/s)]

B) Particle Size Method:

Standard particle size (drop size) measurement protocol:

The particle size distribution of emollient oils in body wash may be characterized by light diffraction measurement using a Malvern Mastersizer® 2000 (Malvern Instruments, Malvern, UK) at ambient conditions. The raw data analysis is conducted by the Mastersizer 2000 software.

The preparation of samples is critical for light scattering measurement. Samples are pre-diluted with deionized water at a ratio of 1:1 to estimate actual shower conditions. The diluted sample is gently blended and loaded into dispersion chamber whereby a well dispersed sample containing representative Petrolatum and other particles was measured.

Experimental Procedure:
1. The Malvern sample dispersion accessories, optical unit and Mastersizer 2000 software are switched on in sequence.
2. Allow the system to automatically clean the sample dispersion accessory, align the optical system, measure the optical background, calculate the size distribution and save the records.
3. For each experiment, 10 experiment cycles are performed with 5 second delay between each cycle. The averaged results are reported
4. Set for normal sensitivity and irregular particle shape to calculate the drop size distribution. The refractive index of petrolatum is 1.4847 and water is 1.3300.
5. Add deionized water to clean the sample accessory until the laser signal intensity reaches 80% or above.
6. Add sample into the accessory until obscuration bar reaches mid value in green region. If sample is very viscous, pre-dispersion may be needed before adding to the accessory.
7. Perform the measurement.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

We claim:

1. A liquid cleansing composition, comprising:
   a. about 5 to 30% by wt. of total synthetic anionic surfactant(s);
   b. about 0.5 to 5% by wt. of total hydrophobically modified acrylate copolymer(s);
   c. about 0.5 to 5% by wt. of total normal C8 to C16 alkyl carboxylic acid(s) wherein at least 90% by wt. of the total normal carboxylic acid(s) is C12 carboxylic acid;
   d. wherein the wt. % ratio range of the total hydrophobically modified acrylate copolymer(s) to the total normal akyl carboxylic acid(s) is about 0.1 to 3;
   e. wherein the composition has a pH range of about 5 to 7.8;
   f. wherein the composition contains less than 0.5% by wt. of total oil(s) and waxes selected from hydrocarbons, triglycerides and silicones with a number average particle size under 1000 microns; and
   g. wherein the Standard Delta zero shear viscosity ratio of liquid cleansing composition is more than 2 in the case of the hydrophobically modified acrylate copolymer(s) effect or more than 30 in the case of the total normal C8 to C16 alkyl carboxylic acid(s)effect.

2. The cleansing composition of claim 1 further comprising total amphoteric surrfactant(s) in the range of 0 to about 5 wt. %.

3. The cleansing, composition of claim 2 wherein the, amphoteric surfactant(s) includes one or more surfactants selected from the group consisting of alkyl betaines, alkyl amino betaines, hydroxysultaines, alkyl amphoacetates; and alkylampho carboxyglycinates.

4. The cleansing composition of claim 1 wherein said anionic surfactant(s) includes one or more surfactants selected from the group consisting of alkyl sulfates, alkyl ether sulfates, alkyl sulfonates, alkylbenzene sulfonates, alkyl succinates, alkyl sulfosuccinates, alkyl olefin sulfonates, alkyl sarcosinates, octoxynol phosphates nonoxynol phosphates, alkyl taurates, polyoxyethylene sulfates, polyoxyethylene isethionates, alkyl carboxylates, and alkyl ether carboxylates or blends thereof.

5. The cleansing composition of claim 1 wherein said at least one acrylate copolymer includes one or more copolymers containing at least one monomer selected from the group consisting of methacrylic acid, acrylic acid, amino acrylic acid, an acrylic acid ester of a C8-30 alkyl, alkylaryl, aryl, heterocyclic, alkoxyl, alkoxyl alkyl ester of a C8-30 alkyl or alkenyl; either substituted or unsubstituted; a methacrylic acid ester of a C8-C30 alkyl, alkylaryl, aryl, heterocyclic, alkoxyl, alkoxyl alkyl ester of a C8-30 alkyl, or alkenyl; either substituted or unsubstituted; a C1-4 alkyl acrylate, and a C1-4 methacrylate; either substituted or unsubstituted.

6. The cleansing composition of claim 1 further comprising insoluble component(s) selected from the group consisting of glass beads, plastic beads, hydrophobic, organic materials, hydrophobic inorganic materials, crystalline solids, air and gas bubbles or blends thereof.

7. The cleansing composition of claim 1 further comprising a solid particulate optical modifier with an average diameter of at least about 30 microns.

8. The cleansing composition of claim 1 further comprising exfoliant particles greater about 50 microns in average diameter at a concentration or less than about 10% by wt.

9. The cleansing composition of claim 1 further comprising an active agent(s) that are present in the range of about 0.01 to 50% by wt.

* * * * *